US008058011B2

(12) United States Patent
Kojima et al.

(10) Patent No.: US 8,058,011 B2
(45) Date of Patent: Nov. 15, 2011

(54) METHOD FOR THE MEASUREMENT OF ENDOCRINE SUBSTANCES IN AN ANALYTE

(75) Inventors: Masaaki Kojima, Shibukawa (JP); Tatsuyuki Hachisu, Shibukawa (JP)

(73) Assignee: Shibayagi Co., Ltd., Shibukawa-shi (JP)

( * ) Notice: Subject to any disclaimer, the term of this patent is extended or adjusted under 35 U.S.C. 154(b) by 596 days.

(21) Appl. No.: 11/988,063

(22) PCT Filed: Nov. 22, 2005

(86) PCT No.: PCT/JP2005/021443
§ 371 (c)(1),
(2), (4) Date: Dec. 28, 2007

(87) PCT Pub. No.: WO2007/000832
PCT Pub. Date: Jan. 4, 2007

(65) Prior Publication Data
US 2009/0176252 A1    Jul. 9, 2009

(30) Foreign Application Priority Data
Jun. 29, 2005   (JP) ................................. 2005-190003

(51) Int. Cl.
*G01N 33/53*   (2006.01)
(52) U.S. Cl. ........ 435/7.1; 435/7.94; 435/961; 435/962; 436/817; 436/825

(58) Field of Classification Search ................... 436/817
See application file for complete search history.

(56) References Cited

U.S. PATENT DOCUMENTS

| 5,691,150 A | 11/1997 | Mori et al. |
| 6,607,891 B1 | 8/2003 | Takada et al. |
| 2003/0087326 A1* | 5/2003 | Mapes et al. ................. 435/7.93 |

FOREIGN PATENT DOCUMENTS

| JP | 2-91572 A | 3/1990 |
| JP | 3-134567 A | 6/1991 |

OTHER PUBLICATIONS

Insulin-like growth factor—Britannica Online Encyclopedia.*

* cited by examiner

*Primary Examiner* — David A Saunders
(74) *Attorney, Agent, or Firm* — Birch, Stewart, Kolasch & Birch, LLP

(57) ABSTRACT

Methods for measuring an endocrine substance, such as feline insulin, in a biological sample taken from an animal with high accuracy, rapidity and brevity. The methods involve pre-treating a biological sample by removing an autoantibody bound to an endocrine substance present in a sample and measuring the endocrine substance after the pre-treatment. The methods can be used to measure autoantibody bound to an endocrine substance in the sample. Methods for diagnosis and treatment of diseases associated with endocrine substances are disclosed involving measuring an autoantibody value for an endocrine substance in a biological sample.

3 Claims, 7 Drawing Sheets

Fig. 1

Weigh 1 mg of CNBr-activated Sepharose ™ 4B (Amersham)
↓
Allow to stand overnight in 1 mM HCl to swell
↓
Wash with 0.1 M CB (pH 8.5)
↓
Couple 50 mg of bovine insulin (Sigma) having an amino acid sequence different from that of feline insulin by one amino acid on gel using 10 ml of 0.1 M CB (pH 9.6) after dissolving in 70% ethanol-1 mM
↓
Block with 0.1 M Tris-HCl (pH 7.8)
↓
Wash with 10 mM PBS
↓
Prepare Insulin-conjugated affinity column Prepare a dilute solution of feline plasma (100 μl) with 10 mM PBS (10 ml)
↓
Apply said dilute solution to said insulin-conjugated affinity column
　　↓　using 10 mM PBS as conjugation buffer; and
　　↓　using 0.1 M glycine - HCl (pH 2.5) as elution buffer
Recover pass fractions and elution fractions
↓
Adjust pH close to neutral
↓
Recover elution fraction
↓
Subject non-insulin-conjugated feline autoantibody and bovine insulin to antigen-antibody reaction in the elution fraction to confirm antigen-antibody reaction with anti-feline IgG (H+L)

METHOD FOR THE MEASUREMENT OF ENDOCRINE SUBSTANCES IN AN ANALYTE

This application is a National Phase of PCT International Application, PCT/JP2005/021443 filed on Nov. 22, 2005 and claiming priority of 2005-190003 filed in Japan on Jun. 29, 2005.

TECHNICAL FIELD

The present invention relates to a method for the measurement of an endocrine substance in an analyte, in particular a feline blood analyte and so on. More particularly, the present invention relates to a method for the measurement of the endocrine substance such as insulin and so on in an analyte such as a feline blood analyte or the like in order to diagnose and treat diseases including, for example, feline diabetes and so on.

BACKGROUND TECHNOLOGY

For the diagnosis and treatment of diseases, it is required to identify the diseases, for example, by identifying the kind of substances causing the diseases or associated therewith and measuring a quantitative variation in such substances or investigating susceptibility thereto. Among those diseases, metabolic syndromes are becoming a great social issue because they may be caused by a change of life style including a habit of eating food, that is, a habit of eating a high caloric food with a high content of proteins, carbohydrates, and/or fats . . . and, in addition thereto, by a lack of exercise due to a change of life environment. Particularly, diabetes is causing a serious problem because a number of patients with diabetes mellitus as well as potent people with a risk of causing diabetes are increasing rapidly. In order to diagnose and treat human diabetes mellitus, an amount of human insulin, an endocrine substance of diabetes-associated substances, in blood has to be measured, and the measurement of amounts of human insulin is conducted as a routine check-up at hospitals, clinics and so on.

Recently, in addition to the human being, pet animals such as cats, dogs and so on are causing to occur diseases corresponding to metabolic syndromes like the human being, and a number of pet animals with such diseases is also increasing rapidly due to a change in raising circumstances. For example, diabetes mellitus and so on is increasing among pet animals, which may be caused by feeding food with a high content of proteins, carbohydrates, and/or fats . . . and high calories, such as pet food or the like, and by a lack of exercise due to raising in a narrow room space. It is needless to say that an amount of feline insulin in a feline blood analyze has to be measured in order to diagnose and treat feline diabetes mellitus.

Now, one of the issues is, however, that currently there is no practical method for measuring feline insulin itself in a feline blood analyte. Therefore, feline insulin is currently measured in accordance with a method for the measurement of human insulin (see Patent Publication 1 for example). As a matter of course, this human insulin measurement method cannot measure an accurate amount of the feline insulin because feline insulin is not used as a standard substance so that a difference in reactivity with an antibody can be observed due to a difference in the amino acid sequence between feline insulin and human insulin. Moreover, the current human insulin measurement method has the big problem because it uses a radioactive substance so that there is a concern about a pollution of environment due to radioactive contamination and a disposal of the radioactive substances after the use for measurement. In addition, as the feline insulin cannot be measured directly by this current system, the diagnosis of feline diabetes is conducted simply by a close-up of conditions and measurement of a sugar level of blood and urine. In such a current situation, it is practically impossible to diagnose whether the feline diabetes is caused to occur due to a problem witi the function of the organ or a problem with the function of an insulin carrier or an insulin receptor in blood. Therefore, the big problem encountered with the current diagnosis and treatment of feline diabetes is that an appropriate treatment of feline diabetes cannot be carried out because an accurate cause of the feline diabetes cannot be determined. Particularly, in order to appropriately diagnose and treat diseases of animals, the method for directly measuring endocrine substances associated with such diseases has to be determined.

In this description, for brevity of explanation of the subject matter of the present invention, feline is illustrated as an object to be analyzed and feline insulin is illustrated as an endocrine substance in an analyte of the object to be analyzed. It is to be understood, however, that the object to be analyzed and the endocrine substance are not interpreted as being limited to the feline and the feline insulin and it is needless to say that any object to be analyzed and endocrine substance can be applied to the present invention as long as they are appropriate for the subject matter of the present invention.

As the method for detecting an antigenic substance in a body fluid such as blood serum and so on or measuring concentrations of the antigenic substance, an immunological measurement is recently being applied increasingly. These methods are well known to the art, and an antigenic substance to be measured can be detected or a concentration of the antigenic substance can be measured, for instance, by labeling the antigenic substance or an antibody with a radioactive substance, forming a complex between the antigenic substance and the antibody, and measuring the labeled component.

(Patent Publication #1) Japanese Patent Publication No. H11-326,322.

SUMMARY OF INVENTION

As a result of extensive studies and review on methods for measuring endocrine substances of animals, it has been found by the present inventors that an endocrine substance such as feline insulin or the like present in an analyte of an animal such as feline or the like can be measured in the analyte treated previously to remove an autoantibody with the endocrine substance bound thereto from the analyte. The present invention has been completed from this finding.

Therefore, the present invention has the object to provide a method for measuring an endocrine substance in an analyte, which comprises measuring the endocrine substance such as feline insulin in a blood analyte of an animal such as feline or the like accurately and rapidly by removing an autoantibody bound to the endocrine substance such as feline insulin or the like.

The present invention has another object to provide a method for removing an autoantibody which comprises removing the autoantibody bound to the endocrine substance from the analyte by adding an acid to the analyte.

The present invention has a further object to provide a method for the measurement of an antibody value of an autoantibody by measuring the antibody value of the autoantibody bound to the endocrine substance in the analyte.

The present invention has a still further object to provide a method for the measurement of the endocrine substance which comprises measuring the endocrine substance in an analyte pretreated by the analyte pre-treatment method.

The present invention has a still further object to provide a method for diagnosis and treatment of a disease associated with the endocrine substance, which comprises diagnosing the disease by measuring the antibody value of the autoantibody of the endocrine substance in the analyte by means of the autoantibody value measurement method.

The present invention has a still further object to provide a method of assessment of the diagnosis method or the treatment method by the autoantibody value measurement method.

The present invention has a still further object to provide a diagnosis method and a treatment method, which comprises combining the autoantibody value measurement method with the method for the measurement of the endocrine substance.

The present invention has a still further object to provide a kit for the measurement of the endocrine substance, which can measure the endocrine substance, preferably feline insulin.

In order to achieve the above objects, in a one aspect, the present invention provides a method for the measurement of an endocrine substance such as feline insulin or the like in a blood analyte of an animal such as feline or the like, which comprises measuring the endocrine substance in the analyte accurately and rapidly by removing an autoantibody bound to the endocrine substance from the analyte.

In another aspect, the present invention provides a method for the pre-treatment of the analyte, which comprises removing the autoantibody bound to the endocrine substance from the analyte.

In a further aspect, the present invention provides a method for removal of the autoantibody, which comprises separating the autoantibody bound to the endocrine substance in the analyte and removing the autoantibody bound thereto from the analyte by adding an acid to the analyte.

In a still further aspect, the present invention provides a method for the measurement of a value of an autoantibody, which comprises measuring the value of the autoantibody of the autoantibody bound to the endocrine substance in the analyte.

In a still further aspect, the present invention provides a method for the measurement of the endocrine substance, which comprises measuring the endocrine substance in the analyte pre-treated by the analyte pre-treatment method.

In a still further aspect, the present invention provides a diagnosis method or a treatment method, which comprises diagnosing qr treating a disease associated with the endocrine substance by measuring the value of the autoantibody to the endocrine substance in the analyte by means of the autoantibody value measurement method.

In a still further aspect, the present invention provides an assessment method which comprises assessing the diagnosis method or the treatment method by means of the autoantibody value measurement method.

In another aspect, the present invention provides a diagnosis method and a treatment method, which comprises combining the autoantibody value measurement method with the endocrine substance measurement method.

In another aspect, the present invention provides a kit for measuring the endocrine substance, preferably feline insulin, which is capable of measuring the endocrine substance.

The method for the measurement of substances such as human insulin has so far been applied to measurement of endocrine substances such as feline insulin and so on in an analyte of an animal such as feline and so on. It is now to be noted here that the present invention provides a method that can directly measure an endocrine substance such as feline insulin or the like accurately and rapidly. Further, the endocrine substance measurement method according to the present invention is provided with the great advantages in terms of handling with great conciseness because it can utilize an enzyme immune measurement method ordinarily utilized in the art involved without using any radioactive substance.

BRIEF DESCRIPTION OF THE DRAWINGS

FIG. 1 is a flow chart showing a method for determining an anti-insulin autoantibody in a feline blood sample.

BEST MODES FOR CARRYING OUT THE INVENTION

Figure 2:
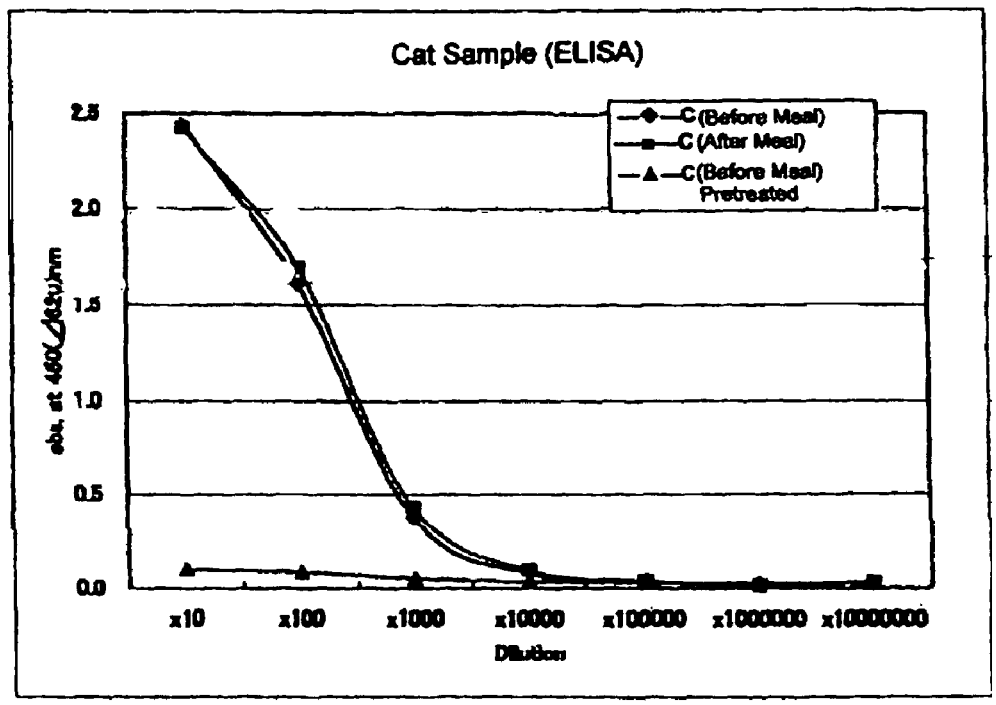
FIG. 2 is a graph showing the result of measurement of anti-feline insulin autoantibody (an IgG-insulin complex).

In order to diagnose the presence or absence of a certain disease and treat it, endocrine substances associated with the disease are required to be measured. For example, in order to diagnose human diabetes mellitus, it is needed to measure an amount of human insulin, an endocrine substance that is closely associated with the human diabetes mellitus. Likewise, it is essential to measure an amount of feline insulin in a blood analyte of an animal such as feline for diagnosing and treating feline diabetes mellitus.

An autoantibody to an endocrine substance such as insulin or the like may be secreted in blood of an animal such as feline or the like, and a portion of the autoantibody is present in such a state that it is bound to the endocrine substance. In order to measure the endocrine substance in a blood analyte, it is needed to remove the autoantibody bound to the endocrine substance from the blood analyte before measuring the collected blood analyte. In other words, the endocrine substance may be measured by using blood as an analyte in which the endocrine substance is separated from the autoantibody bound to the endocrine substance. At this end, for example, an anti-insulin feline antibody and an anti-mouse IgG (rheumatoid factor) antibody by measuring a value of an insulin-bound insulin autoantibody and a value of anti-mouse IgG (rheumatoid factor) autoantibody.

On the other hand, a portion of the autoantibody to the endocrine substance such as feline insulin or the like secreted in blood is present in a state in which it is not bound to the endocrine substance. In order to measure the non-bound autoantibody, the autoantibody is adsorbed on an appropriate adsorbent such as a chromatography column or the like and a value of the autoantibody non-bound to the endocrine substance in an eluate from the adsorbent is measured.

Therefore, the measurement of the value of the autoantibody to the endocrine substance such as feline insulin or the like can be applied to, for example, a method for selection of the method for the treatment of a feline with a high blood sugar level or a method for determination of the effect of the treatment thereof or a method for selection of the method for the treatment of a feline with an autoimmune disease or the like or a method for determination of the effect of the treatment thereof.

In order to apply such methods, it is needed to measure an amount of insulin of an individual object to be measured, such as feline or the like. For instance, the measurement of an amount of insulin of a feline individual allows a diagnosis of the kind and type of diseases such as diabetes mellitus or the like. It is to be noted here, however, that the feline insulin has to be free from other interfering substances in a blood analyte in order to measure an accurate amount of the insulin of the feline individual. At this end, it is required to measure a value of the autoantibody of insulin to determine whether a substance bound to insulin is present or not.

Further, in the event that the autoantibody to the endocrine substance such as insulin or the like is detected, the autoantibody thereto has to be removed. In other words, the analyte of an object to be analyzed is to be pre-treated to remove the autoantibody from the analyte. Moreover, it is preferred to confirm the autoantibody to insulin has already been removed from the analyte by measuring a value of the autoantibody to insulin. After the confirmation of the removal of the autoantibody thereto, an amount of insulin in a feline blood analyte is then measured.

Moreover, the present invention can be applied to a selection of an insulin preparation and a route of administration of the insulin preparation by measuring the anti-insulin autoantibody non-bound to insulin before administration of the insulin preparation. In addition, it can also be applied to a determination of diagnosis and treatment effects of insulin preparations by measuring an insulin autoantibody bound to insulin of a feline individual.

Furthermore, the measurement of an antibody value of the autoantibody to insulin and an antibody value of a mouse antibody to rheumatoid factor as a marker for an autoimmune disease can also be applied to the determination of effects of diagnosis and treatment of the autoimmune diseases.

As an analyte to be used for the present invention, there may be used, for example, an analyte collected from a pet animal such as feline and so on, and such analyte may include, for example, a body fluid such as blood or the like, an organ or a tissue of the organ such as the pancreas or the like. The blood analyte may be total blood or serum or plasma separated from blood, and such serum or plasma analytes may be prepared by separation from the blood analyte by usual techniques.

The endocrine substance to be used as an object to be measured in accordance with the present invention may include, for example, substances which are produced in the organs and tissues, and secreted into body fluids of pet animals such as feline and so on and which act as a marker useful for diagnosis of a morbid state of a certain disease and so on or for treatment of the disease. In the case of feline diabetes mellitus, the endocrine substance may include feline insulin useful for diagnosis and treatment of feline diabetes mellitus.

As a result of review on the possibility of measuring the endocrine substance derived from an animal species as the object to be measured in comparison of the amino acid sequence of the endocrine substance with an amino acid sequence of the endocrine substance of another animal species, it was found that feline insulin can be measured by utilizing insulin of rat as another animal species. In this case, the measurement can be conducted by sandwich method using antibodies to cat insulin A chain and rat insulin B chain.

The amino acid sequences of feline insulin and rat insulin are as follows:

TABLE 1

| (Cat Insulin A chain): | | | | | |
|---|---|---|---|---|---|
| Animal | 1 | 6 | 11 | 16 | 21 |
| Cat | GIVEQ (SQ ID #1) | CCASV (SQ ID #2) | CSLYQ (SQ ID #3) | LEHYC (SQ ID #4) | N (SQ ID #5) |
| Rat I | GIVDQ (SQ ID #6) | CCTSI (SQ ID #7) | CSLYQ (SQ ID #8) | LENYC (SQ ID #9) | N (SQ ID #10) |
| Rat II | GIVDQ (SQ ID #11) | CCTSI (SQ ID #12) | CSLYQ (SQ ID #13) | LENYC (SQ ID #14) | N (SQ ID #15) |

TABLE 2

| (Rat Insulin B chain): | | | | | | |
|---|---|---|---|---|---|---|
| Animal | 1 | 6 | 11 | 16 | 21 | 26 |
| Cat | FVNQH (SQ ID #16) | LCGSH (SQ ID #17) | LVEAL (SQ ID #18) | VLVCG (SQ ID #19) | ERGFF (SQ ID #20) | VTPKA (SQ ID #21) |
| Rat I | FVKQH (SQ ID #22) | LCGPH (SQ ID #23) | LVEAL (SQ ID #24) | VLVCG (SQ ID #25) | ERGFF (SQ ID #26) | VTPKS (SQ ID #27) |
| Rat II | FVKQH (SQ ID #28) | LCGSH (SQ ID #29) | LVEAL (SQ ID #30) | VLVCG (SQ ID #31) | ERGFF (SQ ID #32) | VTPMS (SQ ID #33) |

The reference symbols referred in the above tables are: A is alanine; C is cysteine; D is aspartic acid; E is glutamic acid; F is phenylalanine; G is glycine; H is histidine; I is isoleucine; K is lysine; L is leucine; M is methionine; N is asparagine; P is proline; Q is glutamine; R is arginine; S is serine; T is threonine; V is valine; and Y is tyrosine.

As a result of comparison between the amino acid sequences of feline insulin and rat insulin, it can be presumed that feline insulin can be measured by utilizing rat insulin. Therefore, it can be considered that feline insulin can be measured using a rat insulin ELISA kit.

As described above, for instance, an autoantibody to the endocrine substance is produced in blood of an animal such as feline and so on, and the autoantibody thereto is present in such a state that all the autoantibody is not bound to the endocrine substance while a portion of the autoantibody is bound thereto. The presence of the autoantibody bound to the endocrine substance in a blood analyte makes it difficult to measure the endocrine substance itself in the analyte. Therefore, in order to measure an accurate amount of the endocrine substance in the analyte, the endocrine substance has to be present in the analyte in such a state that the endocrine substance is not bound to the autoantibody. At this end, it is needed, accordingly, to detect the presence or absence of the autoantibody bound to the endocrine substance and measure a value of the autoantibody to the endocrine substance. If the autoantibody bound to the endocrine substance were detected in the analyte, the autoantibody bound to the endocrine substance has to be removed from the analyte.

First, a description will be made regarding the method for the detection of the presence of the substance bound to the endocrine substance by taking ELISA method conventionally used in the art as an example. In this example, feline serum was measured by ELISA using insulin-bound insulin autoantibody and anti-mouse IgG autoantibody.

The insulin-bound autoantibody to insulin may be measured, for example, by adding a feline serum analyte to an immobilized anti-insulin antibody on a plate and reacting the anti-insulin antibody with an antigen in the analyte by an antigen-antibody reaction, and reacting the antibody-antigen complex with a labeled enzyme-conjugated goat anti-feline IgG. After the completion of the reaction, an enzyme substrate is allowed to develop a color and the color development is measured at a given absorbency. On the other hand, the measurement of the anti-mouse IgG autoantibody can also be carried out in substantially the same manner as that of the insulin-bound insulin autoantibody.

As the enzyme used for labeling in ELISA, there may be used generally any enzyme conventionally used for ELISA, and it may include, but may not be limited to, peroxidase, alkali phosphatase, β-D-galactosidase, glucose oxidase, luciferase, esterase, p-D-glucuronidase, and so on. Among these enzymes, peroxidase or alkali phosphatase is preferred from the point of view to achieve a highly sensitive and stable detection. On the other hand, the substrate may appropriately be selected according to the enzyme to be used and include, but may not be limited to, 3,3',5,5'-tetramethylbenzidine or the like in the case of peroxidase, and sodium p-nitro phenyl phosphate or the like in the case of alkali phosphatase.

The detection and quantitative measurement of a product from the above enzyme may be conducted by measuring an absorbency of the product. For instance, the reaction product of 3,3',5,5'-tetramethylbenzidine as the substrate can be measured at absorbency of 450 nm.

The purification of the endocrine substance will then be described by taking feline insulin as an example. For instance, feline insulin in a feline pancreas analyte can be purified by adding a hydrochloric acid solution to the analyte to form a homogenate and purifying the resulting homogenate by usual purification procedures. Feline insulin can be purified in accordance with the known purification procedures for human insulin.

More specifically, feline insulin can be purified, for example, by adding a hydrochloric acid solution to an analyte from the feline pancreas or the like to form a homogenate, separating a supernatant by centrifugation of the resulting homogenate, and subjecting the resulting supernatant to conventional purification procedures such as chromatography or the like. For this purification, it is preferred to use a carrier for purification of biopolymers such as proteins or nucleic acids, e.g., fractogel for example. This carrier is particularly preferred for purification of a large amount of proteins and antibodies because it has a higher capacity for binding proteins and so on, as compared with usual carriers for purification of proteins and so on.

The eluate obtained in the manner as described above can further be subjected to conventional purification procedures such as chromatography or the like and feline insulin can be purified by separating and collecting a fraction having a given peak from the fractions of the eluate. For the chromatography to be used herein, there may be preferably used, for example, a high-performance reverse-phase chromatography column suitable for purification of biomolecules.

The purified feline insulin may then be freeze-dried after confirmation of its molecular weight by means of SDS-PAGE or the like and weighed for use as a first standard product of a kit for measurement of feline insulin.

The anti-insulin autoantibody in a feline blood analyte can be confirmed by means of the method as shown in FIG. 1. As a result of SDS-PAGE electrophoresis of the eluate fraction (2ME+), two bands were confirmed nearby at the molecular weights of approximately 50,000 and 25,000. This is confirmed that the fraction comprises an IgG-type antibody.

A description will then be made regarding the measurement of an analyte such as a feline serum or plasma analyte. As described above, feline insulin can be measured using a rat insulin ELISA kit on the basis of the presumption from a comparison between the amino acid sequences of feline insulin and rat insulin. In the event that the rat insulin ELISA kit reacts with feline insulin extracted directly from feline pancreas but it does not react with feline insulin in the serum or plasma analyte, it may be considered that the reaction of the rat insulin ELISA kit with the antibody is obstructed by the autoantibody to feline insulin due to its binding to the feline insulin in the blood analyte. This is considered to happen because the autoantibody to feline insulin is present in feline blood.

It is needed therefore to confirm the presence of the autoantibody to insulin in a feline serum or plasma analyte. The insulin autoantibody can be confirmed by using a monoclonal antibody to rat insulin in accordance with the procedures as have been described above.

In the event that the presence of the autoantibody bound to the endocrine substance such as insulin or the like in the analyte is confirmed, the autoantibody bound to the endocrine substance is to be removed from the analyte. After the autoantibody bound to the endocrine substance has been removed from the analyte, the endocrine substance can be extracted and then measured accurately and rapidly.

A description will now turn to the procedures for removing the autoantibody bound to the endocrine substance from a blood analyte in which the autoantibody bound thereto is present.

In order to remove the autoantibody bound to the endocrine substance from the blood analyte, first, the blood analyte is made acidic to terminate an antigen-antibody reaction for the binding of the endocrine substance to the autoantibody, thereby allowing a separation of the endocrine substance from the antibody. The analyte may be acidified with an acidic substance including, but being not limited to, an inorganic acid such as hydrochloric acid or sulfuric acid or an organic acid such as acetic add. Among the acids, the inorganic acid is preferred and, more specifically, it is preferred to use 0.5 M to 2 M hydrochloric acid or 0.25 M to 1 M sulfuric acid. An amount of the acid to be added to the analyte may be from a 1/50-fold to 10-fold amount, preferably a 1/20-fold to one-fold amount, with respect to the total amount of the analyte, although the amount of the acid is not restricted to a particular one and it may vary with the amount of the analyte.

After the binding of the autoantibody to the endocrine substance by means of the antigen-antibody reaction is terminated by making the analyte acidic in the manner as described above, the analyte is then added with a protein-precipitation agent to precipitate the autoantibody. The precipitation of the autoantibody bound to the endocrine substance permits a separation of the autoantibody non-bound to the endocrine substance. The protein-precipitation agent may include, but may not be limited to, saturated ammonium sulfate, saturated sodium sulfate and polyethylene glycol. Among the protein-precipitation agent, there may be preferably used saturated ammonium sulfate in a concentration of approximately 30% to 60%, preferably approximately 33% to 55%, or polyethylene glycol 3000-6000 in a concentration of approximately 0.5% to 20%. An amount of the protein-precipitation agent to be added is not limited to a particular one as long as it can precipitate the above protein and may be from approximately 30% to 70%, preferably from approximately 40% to 60% as a final concentration of the protein-precipitation agent. Further, the pH of the analyte may be in the range of approximately pH 3.0 to pH 2.0.

After the addition of protein-precipitation agent, the addition of an ethanolic solution to the analyte can recover the endocrine substance co-precipitated with the autoantibody bound to the endocrine substance. The recovery of the endocrine substance can lead to a simultaneous separation of the autoantibody from the analyte. The ethanolic solution may be in a concentration of from approximately 60% to 95%, preferably from approximately 65% to 80%. The final concentration of ethanol may be from approximately 60% to 80%, preferably from approximately 65% to 75%. Further, the ethanolic solution may be added as a mixture with an acid such as hydrochloric acid.

Undissolved matters are then to be separated from the analyte prepared in the manner as described above. The separation may be effected to separate the undissolved matters (e.g., auto antibodies including the autoantibody bound to the endocrine substance and so on) from a supernatant centrifuged or filtrate filtered by conventional separation procedures including, for example, centrifugation or filtering under given conditions. The resulting supernatant or filtrate can be used as an analyte to be measured. Where the analyte so pre-treated in the above-mentioned manner to remove the autoantibody bound to the endocrine substance therefrom is used as an analyte for analysis, the endocrine substance as the object to be measured present in the analyte can be measured with high accuracy and rapidity.

It is preferred to re-confirm whether the autoantibody bound to the endocrine substance is yet left in the pre-treated analyte from which the autoantibody bound to the endocrine substance has been removed by re-measuring a value of the autoantibody. In the event where the autoantibody bound thereto still remains in the once pre-treated analyte, the remaining autoantibody bound to the endocrine substance is to be removed again from the analyte by repeating the procedures for removing the autoantibody. Once it has been confirmed that no antibody bound to the endocrine substance remained in the analyte, the endocrine substance is detected by measuring the endocrine substance in the analyte.

In accordance with the present invention, the endocrine substance such as insulin and so on present in the pretreated analyte can be measured and detected by conventional techniques including, but being not limited to, sandwich ELISA method customarily used in the art.

More specifically, for instance, a monoclonal antibody to rat insulin is immobilized on a plate and a biotin-bound anti-insulin monoclonal antibody is added to the plate. Then, a feline blood analyte (a pretreated analyte) is added to the plate to cause an antigen-antibody reaction with an antibody corresponding to the endocrine substance such as insulin or the like in the analyte to form an antigen-antibody complex. Thereafter, avidin bound with an enzyme such as peroxidase or the like is added to the resulting complex and a color is developed with the above enzyme substrate, and the endocrine substance such as insulin or the like as an object for measurement is measured at a given absorbency.

Therefore, the present invention can briefly and accurately measure the endocrine substance such as feline insulin and so on in the blood analyte of an animal such as feline and so on in a quantitative manner by pre-treating the analyte in accordance with the pre-treatment method according to the present invention.

The present invention further allows a diagnosis and treatment of diseases associated with the endocrine substance, such as diabetes mellitus and so on, by measuring a value of the autoantibody to the endocrine substance such as feline insulin in an analyte such as a feline blood analyte or the like by means of the autoantibody value measurement method. A combination of the autoantibody value measurement method with the endocrine substance measurement method enables a diagnosis and treatment of diseases associated with the endocrine substances.

In addition, the present invention provides a kit for use in measurement of the endocrine substance, which is capable of measuring the endocrine substances including, but being not limited to, feline insulin and so on. A kit for use in measurement of feline insulin may comprise, for example, an antibody immobilized plate, a feline insulin standard solution, a buffer, biotin-bound antibody to insulin, avidin-bound peroxidase, a color developing solution (e.g., TMB), a reaction terminator (e.g., sulfuric acid), a rinsing liquid and so on.

The following is a description regarding working examples in accordance with the present invention. It is to be noted here, however, that the present invention is not interpreted in any respect as being restricted to the example which follow below and that the examples are described hereinafter merely as a specific illustration of the present invention.

EXAMPLES

Example 1

Purification of Feline Insulin

To a feline pancreas was added 40 ml of a mixture solution of 750 ml of ethanol, 15 ml of concentrated sulfuric acid and 235 ml of DW (4 ml per gram of the tissue), the mixture was homogenized and stirred at 37° C. for 2 hours and centrifuged at 10,000×g for 20 minutes. The resulting supernatant was collected and evaporated to a half volume. The concentrated supernatant was again centrifuged at 10,000×g for 20 minutes. The resulting supernatant was collected and eluted with 50 mM aqueous ammonia solution through fractogel (EMD-SO3-650, Merck). The resulting eluate was adjusted to pH 2.0 with TFA and purified through a reverse-phase chromatography column (RESOURCE RPC; Buffer A: 0.1% TFA (pH 2.0); Buffer B: 0.1% TFA+60% AcCN; Linear Gradient: A→B; Abs. 215 nm). The resulting fraction having a peak at nearby 50% was collected as an insulin fraction and stored as a purified feline insulin solution.

Example 2

Test for confirmation of Reactivity of Antibody with Feline Insulin

The purified feline insulin solution prepared by Example 1 was subjected to a qualitative test by means of dot blot method as will be described hereinafter. A piece of nitro cellulose membrane, 0.5 cm long and 1.5 cm wide, was blotted with 3 μl of physiological saline on the left side, 1.5 μl of purified feline insulin solution at the center, and 3 μl of the supernatant of the feline pancreas homogenate on the right side. The membrane was blocked with 0.05% Block Ace® and then allowed to stand at room temperature for 2 hours. Thereafter, the membrane was washed three times with a mixture of 0.05% Tween® 20 and 10 mM PBS and then reacted with an anti-insulin monoclonal (D3E7) antibody-biotin conjugate (rat insulin ELISA kit) at 4° C. for 15 to 18 hours. After the membrane was re-washed three times with a mixture of 0.05% Tween® 20 and 10 mM PBS, avidin-HRP (horse radish peroxidase) was added and reacted at room temperature for 30 minutes, followed by re-washing three times with a mixture of 0.05% Tween® 20 and 10 mM PBS. The membrane was then subjected to a color development with a diethylene glycol solution of 4-chloro-1-naphthol at room temperature for 90 minutes. The test results indicated that physiological saline caused no reaction, while the purified feline insulin solution and the feline pancreas homogenate supernatant caused a positive reaction.

Example 3

Preparation of Feline Serum/Plasma Samples

Blood samples were collected from feline at 10 minutes each before and after feeding of standard pet food, and serum or plasma was separated by conventional procedures and used as a feline serum sample and a feline plasma sample, respectively.

Measurement of Feline Serum/Plasma Samples

From a result of a comparison of the amino acid sequence of feline insulin with the amino acid sequence of rat insulin (See Table 1: Insulin A chain; Table 2: Insulin B chain), it is presumed that feline insulin can be measured using a rat insulin ELISA kit.

As a control, a feline blood sample without pre-treatment was measured for an insulin concentration (ng/ml), a C-peptide concentration (pg/ml), and albumin concentration (mg/ml) (TIA method). The test results are shown in Table 3-1. Insulin was measured using Lbis® insulin kit, C-peptide using Lbis® C-peptide kit, and albumin using Lbis® albumin kit. On the other hand, the feline sample pre-treated in the manner as will be described in detail hereinafter was measured for an insulin concentration (ng/ml) using Lbis® insulin kit. The results are shown in Table 3-1:

| Sample ID# | State | Insulin Concentration (ng/ml) | C-Peptide Concentration (pg/ml) | Albumin Concentration (mg/ml) |
|---|---|---|---|---|
| A | Before Meal | Not Detected | Not Detected | 89.3 |
|   | After Meal | Not Detected | Not Detected | 84.8 |
| B | Before Meal | Not Detected | Not Detected | 78.5 |
|   | After Meal | Not Detected | Not Detected | 87.5 |
| C | Before Meal | Not Detected | Not Detected | 85.5 |
|   | After Meal | Not Detected | Not Detected | 56.5 |

TABLE 3-2

| Sample ID# | State | Insulin Concentration (ng/ml) |
|---|---|---|
| B | Before Meal | 1.69 |
|   | After Meal | 2.56 |
| C | Before Meal | 3.60 |
|   | After Meal | 5.82 |

Example 4

Measurement of Autoantibody to Feline Insulin (IgG-Insulin Complex)

To each well of a 96-well plate immobilized with a monoclonal antibody to rat insulin was added 50 μl of a feline serum sample which was diluted at seven dilution steps from a 10-fold dilution, and the plate was allowed to react at room temperature for 1 hour followed by washing with a mixture of 0.05% Tween® 20 and 10 mM PBS. To each well of the plate prepared so was then added 50 μl of HRP-bound goat anti-feline IgG, and the plate was reacted at room temperature for 1 hour followed by washing with a mixture of 0.05% Tween® 20 and 10 mM PBS. To each well was added TMB as a color developer in the amount of 50 μl and the plate was reacted at room temperature for 10 minutes, followed by addition of 50 μl of 1 M sulfuric acid to terminate the reaction. The wells were measured for absorbency at 450 nm (620 nm) and the results are shown in Table 4 and FIG. 2.

TABLE 4

| | Absorbency 450 (Δ620) nm (n = 2) | | |
|---|---|---|---|
| Dilution Rate | Sample C (Before Meal) | Sample C (After Meal) | Sample C (Before Meal), Pre-treated |
| ×10 | 2.439 | 2.424 | 0.102 |
| ×10$^2$ | 1.605 | 1.693 | 0.087 |
| ×10$^3$ | 0.371 | 0.427 | 0.052 |
| ×10$^4$ | 0.079 | 0.096 | 0.033 |
| ×10$^5$ | 0.037 | 0.039 | 0.029 |
| ×10$^6$ | 0.020 | 0.016 | 0.026 |
| ×10$^7$ | 0.026 | 0.030 | 0.027 |
| Blank | 0.018 | 0.018 | 0.015 |

Example 5

Figure 3:
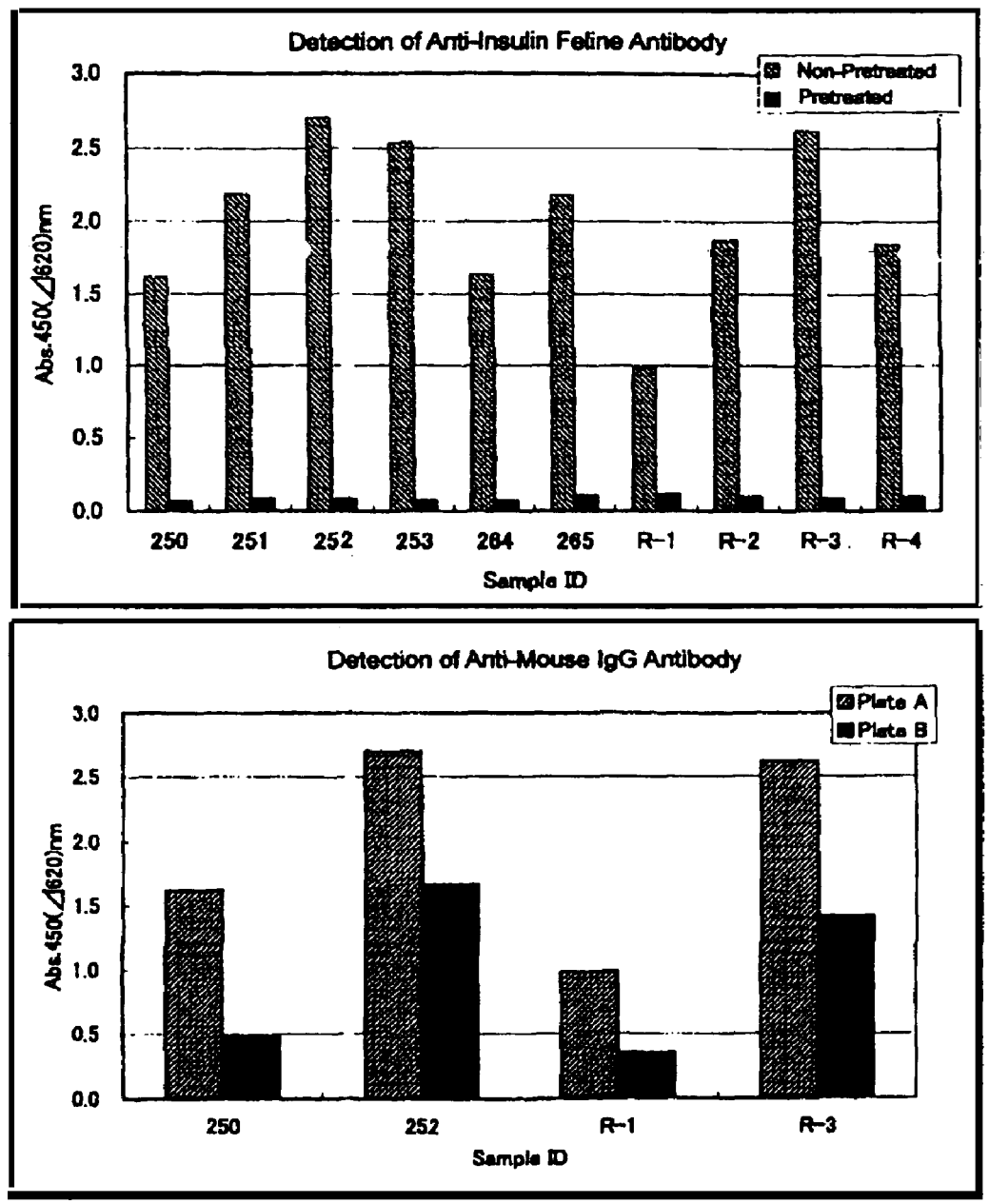
FIG. 3 is a graph showing the result of measurement of a value of an insulin-bound insulin autoantibody and a value of an anti-mouse-IgG antibody.

Measurement of Values of Insulin-Bound Insulin Autoantibody and Anti-Mouse-IgG Antibody in Non-Pretreated Blood Samples Each well of a plate was coated with anti-insulin antibody (Plate A) and with mouse IgG (Plate B). To each well of the plates was added 50 μl of a non-pretreated feline blood sample (10 samples), and the plates were allowed to stand at room temperature for 1 hour, followed by three-time washing with a buffer solution (10 mM PBS). Then, 50 μl of HRP-bound goat anti-feline IgG was added to each well and the plate was then allowed to stand at room temperature for 1 hour, followed by three-time washing with 10 mM PBS. Then, 50 μl of 3,3',5,5'-tetramethyl benzidine (TMB) was added to each well and thereafter 1 M sulfuric acid was added by 50 μl to each well to terminate the reaction. The plate was then measured for absorbency at 450/620 nm. The results are shown in Table 5 and FIG. 3.

Example 6

Measurement of Values of Insulin-Bound Insulin Autoantibody and Anti-Mouse-IgG Antibody in Pretreated Blood Samples Corresponding to Those of Example 5

In substantially the same manner as Example 5, each well of a plate was coated with anti-insulin antibody (Plate A) and with mouse IgG (Plate B). To each well of the plates was added 50 μl of a pretreated feline blood sample (10 samples), and the plates were allowed to stand at room temperature for 1 hour, followed by three-time washing with a buffer solution (10 mM PBS). Then, 50 μl of HRP-bound goat anti-feline IgG was added to each well and the plate was then allowed to stand at room temperature for 1 hour, followed by three-time washing with 10 mM PBS. Then, 50 μl of 3,3',5,5'-tetramethyl benzidine (TMB) was added to each well and thereafter 1 M sulfuric acid was added by 50 μl to each well to terminate the reaction. The plate was then measured for absorbency at 450/620 nm. The results are shown in Table 5 and FIG. 3.

TABLE 5

| Sample | Plate A | | Plate B (*NT = Not Tested) | |
|---|---|---|---|---|
| ID# | Not Pre-treated | Pre-treated | Not Pre-treated | Pre-treated |
| 1 | 1.618 | 0.070 | 0.485 | NT |
| 2 | 2.184 | 0.086 | NT | NT |
| 3 | 2.701 | 0.084 | 1.661 | NT |
| 4 | 2.533 | 0.069 | NT | 0.019 |
| 5 | 1.630 | 0.067 | NT | NT |
| 6 | 2.180 | 0.106 | NT | NT |
| 7 | 0.982 | 0.114 | 0.348 | 0.020 |
| 8 | 1.871 | 0.093 | NT | NT |
| 9 | 2.616 | 0.089 | 1.414 | NT |
| 10 | 1.840 | 0.098 | NT | NT |

(n = 2)

Example 7

Measurement by Feline Serum Insulin-Sepharose Chromatography

Three samples used in Examples 5 and 6 (Sample #5 (as referred to as Sample 264 in the drawing); Sample #7 (as referred to as Sample R-1 in the drawing); and Sample #8 (as referred to as Sample R-2 in the drawing)) were used for measurement.

Figure 4:
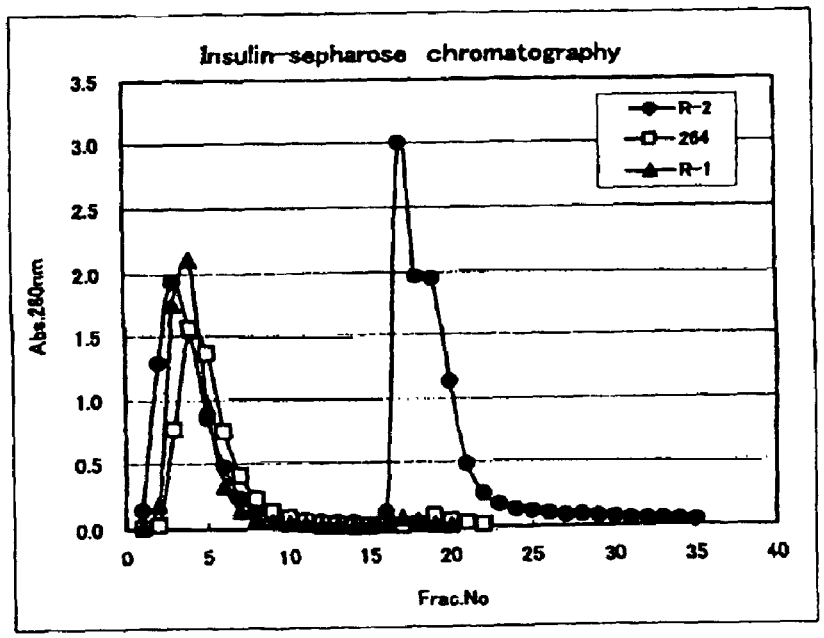
FIG. 4 is a graph showing the result of measurement by a feline serum-insulin-sepharose chromatography.

Each sample (10 µl) was diluted with buffer (10 mM PBS) to 10 ml. The resulting solution was injected into a bovine insulin-bound Sepharose column and chromatography was carried out using 10 mM PBS as a binding buffer solution and 0.1 M glycine-HCl solution (pH 2.5) as an eluting buffer solution at a rate of 1 ml/cycle. A pass fraction and an eluate fraction was each collected and measured for a value of anti-insulin antibody and RF-IgG after a pH adjustment to a neutral range. The results are shown in Table 6-1 (Sample #5), Table 6-2 (Sample #7) and Table 6-3 (Sample #8). Table 4 is a graph showing the above results. In FIG. 4, Sample #5 is represented as Sample 264, Sample #7 as Sample R-1, and Sample #8 as Sample R-2.

TABLE 6-1

| Fraction # | 1 | 2 | 3 | 4 | 5 |
|---|---|---|---|---|---|
| 280 nm | 0.013 | 0.028 | 0.772 | 1.565 | 1.371 |
| Fraction # | 6 | 7 | 8 | 9 | 10 |
| 280 nm | 0.754 | 0.410 | 0.228 | 0.134 | 0.083 |
| Fraction # | 11 | 12 | 13 | 14 | 15 |
| 280 nm | 0.054 | 0.037 | 0.031 | 0.017 | 0.020 |
| Fraction # | 16 | 17 | 18 | 19 | 20 |
| 280 nm | 0.019 | 0.017 | 0.024 | 0.090 | 0.052 |
| Fraction # | 21 | | 22 | | |
| 280 nm | 0.033 | | 0.021 | | |

(Fraction #4 & #5: Pass solution pool; Fraction #19: Eluate pool)

TABLE 6-2

| Fraction # | 1 | 2 | 3 | 4 | 5 |
|---|---|---|---|---|---|
| 280 nm | 0.012 | 0.190 | 1.751 | 2.113 | 0.953 |
| Fraction # | 6 | 7 | 8 | 9 | 10 |
| 280 nm | 0.332 | 0.141 | 0.079 | 0.056 | 0.042 |
| Fraction # | 11 | 12 | 13 | 14 | 15 |
| 280 nm | 0.034 | 0.021 | 0.017 | 0.018 | 0.015 |
| Fraction # | 16 | 17 | 18 | 19 | 20 |
| 280 nm | 0.020 | 0.076 | 0.052 | 0.026 | 0.015 |

(Fraction #4 & #5: Pass solution pool; Fraction #17: Eluate pool)

TABLE 6-3

| Fraction # | 1 | 2 | 3 | 4 | 5 |
|---|---|---|---|---|---|
| 280 nm | 0.145 | 1.294 | 1.936 | 1.532 | 0.857 |
| Fraction # | 6 | 7 | 8 | 9 | 10 |
| 280 nm | 0.475 | 0.235 | 0.143 | 0.100 | 0.075 |
| Fraction # | 11 | 12 | 13 | 14 | 15 |
| 280 nm | 0.063 | 0.057 | 0.048 | 0.046 | 0.027 |
| Fraction # | 16 | 17 | 18 | 19 | 20 |
| 280 nm | 0.114 | 3 | 1.968 | 1.981 | 1.135 |
| Fraction # | 21 | 22 | 23 | 24 | 25 |
| 280 nm | 0.482 | 0.257 | 0.176 | 0.137 | 0.117 |
| Fraction # | 26 | 27 | 28 | 29 | 30 |
| 280 nm | 0.100 | 0.087 | 0.084 | 0.076 | 0.073 |
| Fraction # | 31 | 32 | 33 | 34 | 35 |
| 280 nm | 0.057 | 0.054 | 0.052 | 0.047 | 0.042 |

(Fraction #2-#4: Pass solution pool; Fraction #17-#20: Eluate pool)

Figure 5:
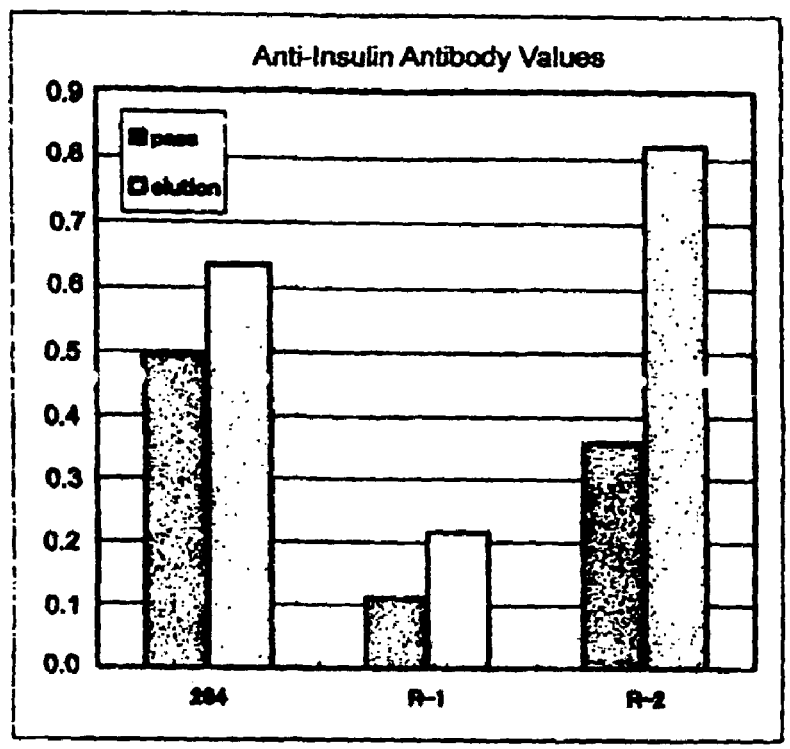
FIG. 5 is a graph showing the result of measurement of a value of an insulin autoantibody.
Figure 6:
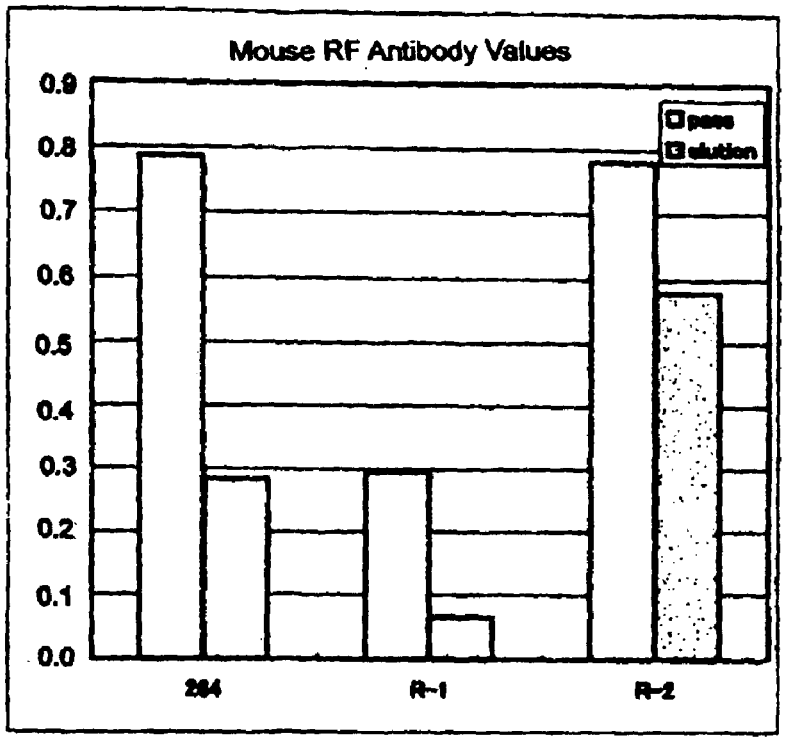
FIG. 6 is a graph showing a value of an antibody to a mouse rheumatoid factor (RF).

FIGS. 5 and 6 show the results of measurement for a value of an insulin autoantibody and a value of mouse rheumatoid factor (RF), respectively, as a marker for an autoimmune disease. In FIG. 5, Sample #5 is represented as Sample 264, Sample #7 as Sample R-1, and Sample #8 as Sample R-2.

Example 8

Tests for Reactivity of Eluate with Insulin by Feline Serum Insulin-Sepharose Chromatography Bovine insulin was added in the amount of 50 µl to each well of a plate and the plate was allowed to stand at room temperature for two hours, followed by washing three times with a buffer solution. Then, 250 µl of 25% Block Ace® was added to each well and the wells were washed three times with buffer, after immobilization. Thereafter, three samples used in Examples 5 and 6, i.s., feline serum-insulin-Sepharose eluates (Sample #5, #7 and #8), were diluted to a given concentration and added by 50 µl to each well, and allowed to react followed by washing three times with buffer. Further, 50 µl of goat anti-feline IgG-HRP was added to each well and the well was washed three times with buffer. The sample was then mixed with 50 µl of TMB and allowed to stand at room temperature for 30 minutes, followed by adding 50 µl of 1 M sulfuric acid to each well and measuring for absorbency at 450/620 nm. As a control, a sample (blank) with no eluate added thereto was used. The results are shown in Table 7-1 (Sample #5), Table 7-2 (Sample #7) and Table 7-3

Figure 7:
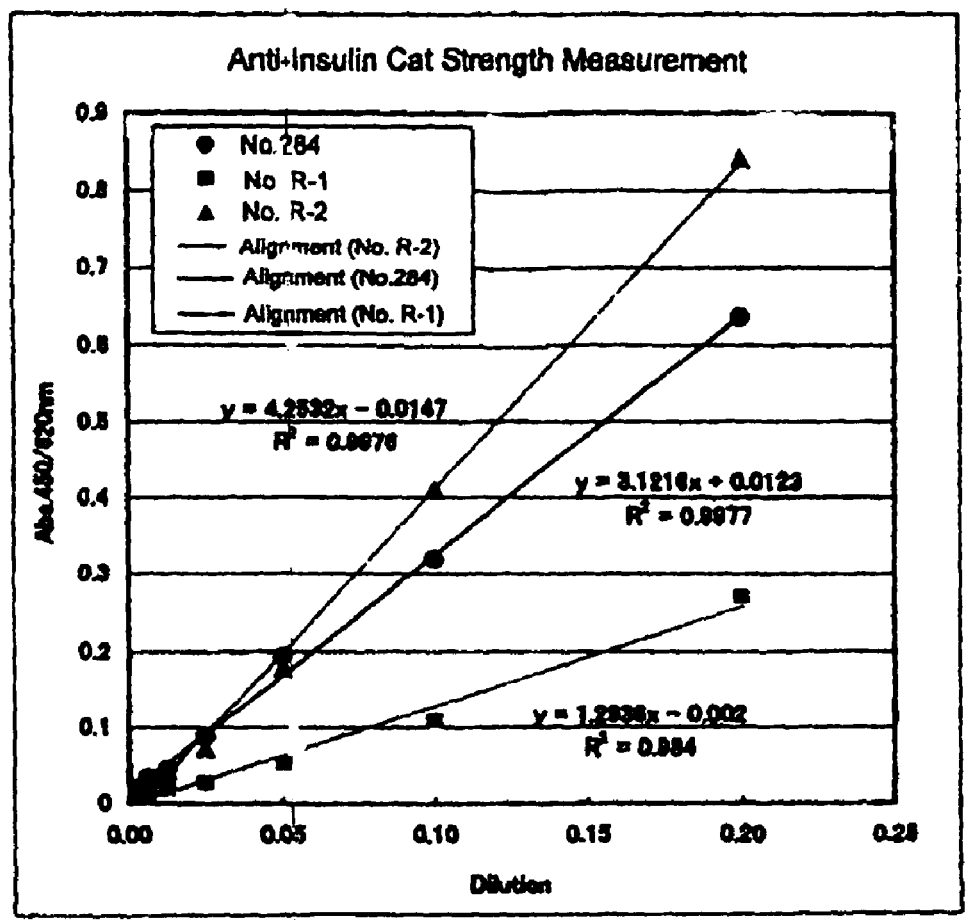
FIG. 7 is a graph showing the result of measurement of a strength of an anti-feline insulin of a gas-chromatography eluate.

(Sample #8) and in FIG. 7. In FIG. 7, Sample #5 is represented as Sample 264, Sample #7 as Sample R-1, and Sample #8 as Sample R-2.

TABLE 7-1

| Dilution | Absorbency 450 (Δ620) nm | | Mean |
|---|---|---|---|
| 0.200 | 0.678 | 0.592 | 0.635 |
| 0.100 | 0.374 | 0.262 | 0.318 |
| 0.050 | 0.260 | 0.125 | 0.192 |
| 0.025 | 0.124 | 0.047 | 0.085 |
| 0.013 | 0.063 | 0.024 | 0.043 |
| 0.006 | 0.047 | 0.017 | 0.032 |
| 0.003 | 0.024 | 0.014 | 0.019 |
| Blank | 0.012 | 0.010 | 0.011 |

TABLE 7-2

| Dilution | Absorbency 450 (Δ620) nm | | Mean |
|---|---|---|---|
| 0.200 | 0.285 | 0.253 | 0.269 |
| 0.100 | 0.113 | 0.103 | 0.108 |
| 0.050 | 0.055 | 0.049 | 0.052 |
| 0.025 | 0.027 | 0.025 | 0.026 |
| 0.013 | 0.018 | 0.018 | 0.018 |
| 0.006 | 0.015 | 0.014 | 0.014 |
| 0.003 | 0.012 | 0.013 | 0.012 |
| Blank | 0.009 | 0.010 | 0.010 |

TABLE 7-3

| Dilution | Absorbency 450 (Δ620) nm | | Mean |
|---|---|---|---|
| 0.200 | 0.859 | 0.826 | 0.843 |
| 0.100 | 0.428 | 0.391 | 0.410 |
| 0.050 | 0.183 | 0.175 | 0.179 |
| 0.025 | 0.067 | 0.075 | 0.071 |
| 0.013 | 0.040 | 0.046 | 0.043 |
| 0.006 | 0.023 | 0.023 | 0.023 |
| 0.003 | 0.017 | 0.017 | 0.017 |
| Blank | 0.011 | 0.011 | 0.011 |

Example 9

Pre-Treatment of Feline Blood Sample

To a feline blood sample (serum or plasma) was added a 1/10 (v/v) volume of 1 M hydrochloric acid, and the mixture was stirred. Then, a saturated ammonium sulfate solution (pH 2.5) was added to reach a final concentration of 50%, and the mixture was stirred at room temperature for 10 minutes, followed by adding an ethanol-10 mM HCl solution to reach a final ethanol concentration of 70%. The resulting mixture was stirred at room temperature for 10 minutes and centrifuged at 2,800 rpm at 4° C. for 15 minutes or filtered to remove undissolved matters. The resulting supernatant or filtrate was collected as a sample for use in measurement. This process removed the autoantibody to insulin from the feline blood sample.

Example 10

Recovery of Sample after Treatment

To a feline serum sample was added insulin extracted from feline pancreas and purified, and the sample was pre-treated in the same manner as above. A recovery rate of insulin was measured (see Table 8). The measured value was a value translated into a solution amount in unit of pg/ml.

TABLE 8

| Amount of Insulin Added | Measured Value | Recovered Amount | Recovery Rate (%) |
|---|---|---|---|
| 0 | 777 | — | — |
| 250 | 978 | 201 | 80 |
| 500 | 1,159 | 382 | 76 |
| 1,000 | 1,535 | 758 | 76 |

(n = 5)

Example 11

Comparison of Feline and Rat Insulin Standards

1. Preparation of standard feline Insulin Sample Solution

The feline insulin preparation purified from the pancreas was diluted with 10 mM PBS to make up solutions with insulin concentration of 2,500 pg/ml, 1,250 pg/ml, 625 pg/ml, 313 pg/ml, 156 pg/ml, 78 pg/ml, and 39 pg/ml. The rat insulin standard solutions were also prepared in the same manner.

2. Preparation of 96-Well Plate Immobilized with Monoclonal Antibody to Rat Insulin A 96-well plate was washed three times with a mixture of 0.05% Tween® 20 and 10 mM PBS, and 100 μl of anti-rat insulin monoclonal antibody was added to each well of the plate to prepared a 96-well plate immobilized with the monoclonal antibody to rat insulin.

3. Method for Measurement

Figure 8:
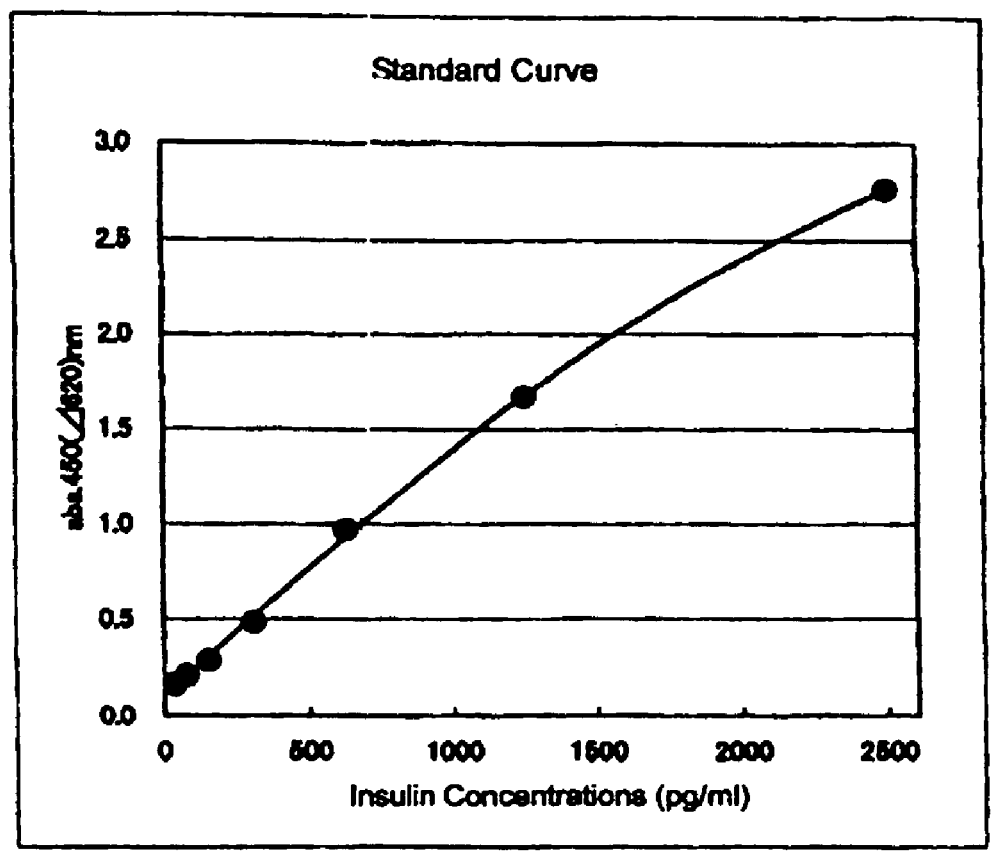
FIG. 8 is a graph showing a standard curve of feline insulin.
Figure 9:
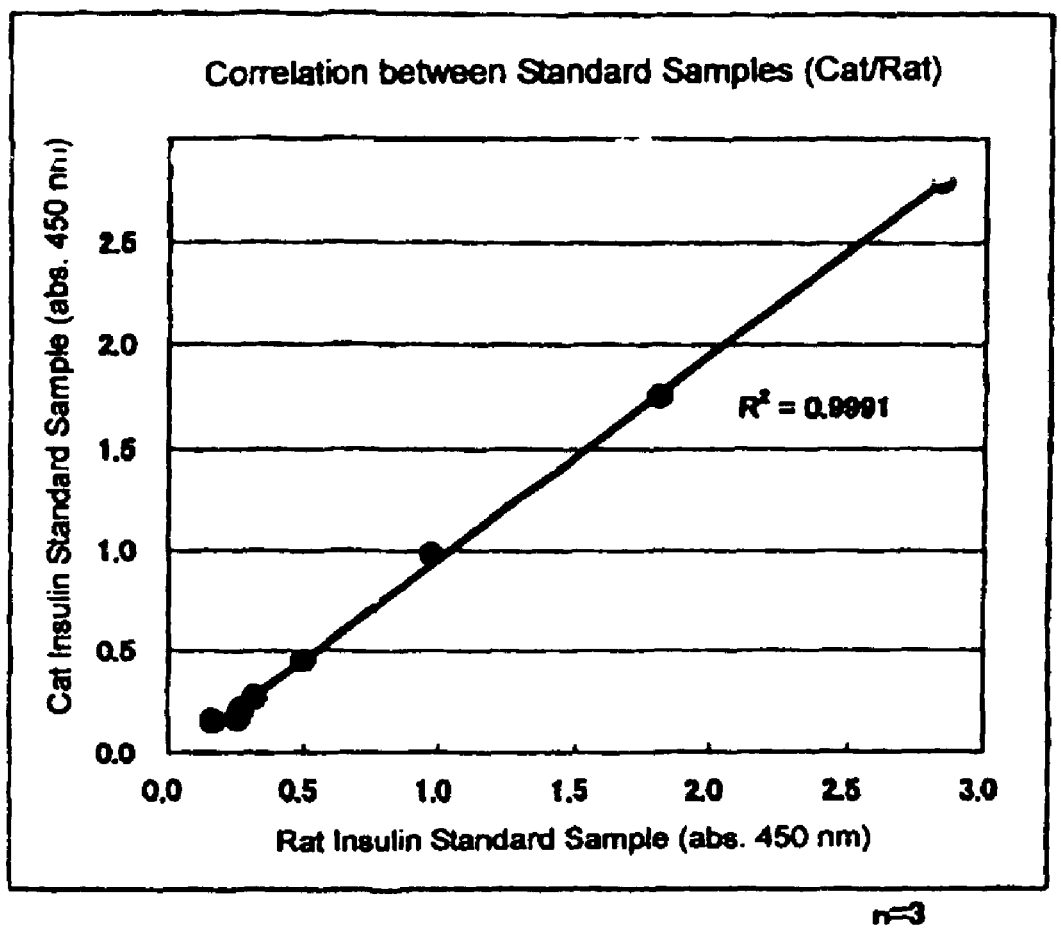
FIG. 9 is a graph showing a Correlation of a standard feline insulin with a standard rat insulin.

To each well of the 96-well plate immobilized with the monoclonal antibody to rat insulin were added 100 μl of biotin-bound anti-rat insulin monoclonal antibody and 10 μl of standard feline insulin solution or rat insulin standard solution, and the mixture was allowed to react at 20 to 25□ for 2 hours. After washing the mixture three times with 10 mM PBS containing 0.05% Tween® 20, 100 μl of HRP-bound streptavidin solution was added to each well, and allowed to react at 20 to 25□ for 30 minutes. After washing the well-plate for three times with the washing solution described above, 100 μl of TMB as a color developer was added to each well and the plate was allowed to react at 20 to 25□ for 30 minutes. Thereafter, 100 μl of 1M sulfuric acid was added to terminate the reaction. Each well was measured for absorbency at 450/620 nm, and the result is shown as a standard curve in FIG. 8. Further FIG. 9 shows a correlation of a standard feline insulin preparation with a standard rat insulin preparation.

Example 12

Measurement of Feline Blood Samples

In substantially the same manner as Example 11, to each well of a plate immobilized with the monoclonal antibody to rat insulin were added 100 μl of biotin-bound anti-rat insulin monoclonal antibody and 10 μl of standard solution prepared by serial dilution of feline standard insulin starting from 10,000 pg/ml or feline sample serum (Sample #1-#10) with or without pretreatment. Then following the assay procedure described above, Assay values of feline insulin in the feline serum samples was calculated from their absorbency using the standard curve. The results are shown in Table 9-1 (standard insulin solution) and in Table 9-2 (feline serum).

TABLE 9-1

| pg/ml | Absorbency 450 (Δ620) nm | | Mean | SD | CV (%) |
|---|---|---|---|---|---|
| 10,000 | 2.166 | 2.125 | 2.145 | 0.029 | 1.35 |
| 5,000 | 1.048 | 0.980 | 1.014 | 0.048 | 4.77 |
| 2,500 | 0.476 | 0.445 | 0.450 | 0.022 | 4.68 |
| 1,250 | 0.200 | 0.187 | 0.193 | 0.009 | 4.87 |
| 625 | 0.085 | 0.083 | 0.084 | 0.002 | 1.85 |
| 313 | 0.044 | 0.041 | 0.042 | 0.002 | 4.88 |
| 156 | 0.029 | 0.030 | 0.030 | 0.001 | 2.85 |
| 0 | 0.022 | 0.021 | 0.021 | 0.001 | 4.63 |

(n = 2)

TABLE 9-2

| | Measurement Results (pg/ml) | |
|---|---|---|
| Sample ID # | Not Pre-treated | Pre-treated |
| 1 | ND | 332 |
| 2 | ND | 424 |
| 3 | ND | 524 |
| 4 | ND | 501 |
| 5 | ND | 417 |
| 6 | ND | 622 |
| 7 | ND | 562 |
| 8 | ND | 629 |
| 9 | 3.36 | 546 |
| 10 | ND | 430 |

(n = 2)

INDUSTRIAL APPLICABILITY

The method for the measurement for human insulin has so far been applied, for example, to measuring endocrine substances themselves such as feline insulin and so on in an feline blood analyte of an animal. The present invention has the merit that the endocrine substances themselves such as feline insulin and so on can be measured more accurately and instantly. The present invention has also the merit that it can be handled with an extreme brevity because no radioactive substance is used and an enzymatic immunological method ordinarily used in the art involved can be applied.

The method for the measurement of the endocrine substances according to the present invention can accurately, rapidly and briefly measure the endocrine substances such as feline insulin and so on in an analyte, e.g., a blood analyte, of an animal such as cat, etc., in order to diagnose and treat diseases associated with the endocrine substance, e.g., diabetes mellitus. In addition, the method of the present invention is very convenient because it uses established procedures of the measurement methods conventionally used in the art involved.

The invention claimed is:

1. A method for pre-treatment of a sample comprising:
   removing an autoantibody bound to feline insulin present in the sample prior to measuring the feline insulin in the sample.

2. The method for pre-treatment of the sample as claimed in claim 1, further comprising adding saturated ammonium sulfate, saturated sodium sulfate or polyethylene glycol to said sample to precipitate an autoantibody non-bound to the feline insulin after removing the autoantibody bound thereto.

3. A method for the measurement of feline insulin, comprising measuring the feline insulin by a quantitative measurement method in a sample pre-treated by said method as claimed in claim 1.

* * * * *

SEQUENCE LISTING

```
<160> NUMBER OF SEQ ID NOS: 33

<210> SEQ ID NO 1
<211> LENGTH: 5
<212> TYPE: PRT
<213> ORGANISM: Feline

<400> SEQUENCE: 1

Gly Ile Val Glu Gln
1               5

<210> SEQ ID NO 2
<211> LENGTH: 5
<212> TYPE: PRT
<213> ORGANISM: Feline

<400> SEQUENCE: 2

Cys Cys Ala Ser Val
1               5

<210> SEQ ID NO 3
<211> LENGTH: 5
<212> TYPE: PRT
<213> ORGANISM: Feline

<400> SEQUENCE: 3

Cys Ser Leu Tyr Gln
1               5

<210> SEQ ID NO 4
<211> LENGTH: 5
<212> TYPE: PRT
<213> ORGANISM: Feline

<400> SEQUENCE: 4
```

```
Leu Glu His Tyr Cys
1               5

<210> SEQ ID NO 5
<211> LENGTH: 1
<212> TYPE: PRT
<213> ORGANISM: Feline

<400> SEQUENCE: 5

Asn
1

<210> SEQ ID NO 6
<211> LENGTH: 5
<212> TYPE: PRT
<213> ORGANISM: Rat

<400> SEQUENCE: 6

Gly Ile Val Asp Gln
1               5

<210> SEQ ID NO 7
<211> LENGTH: 5
<212> TYPE: PRT
<213> ORGANISM: Rat

<400> SEQUENCE: 7

Cys Cys Thr Ser Ile
1               5

<210> SEQ ID NO 8
<211> LENGTH: 5
<212> TYPE: PRT
<213> ORGANISM: Rat

<400> SEQUENCE: 8

Cys Ser Leu Tyr Gln
1               5

<210> SEQ ID NO 9
<211> LENGTH: 5
<212> TYPE: PRT
<213> ORGANISM: Rat

<400> SEQUENCE: 9

Leu Glu Asn Tyr Cys
1               5

<210> SEQ ID NO 10
<211> LENGTH: 1
<212> TYPE: PRT
<213> ORGANISM: Rat

<400> SEQUENCE: 10

Asn
1

<210> SEQ ID NO 11
<211> LENGTH: 5
<212> TYPE: PRT
<213> ORGANISM: Rat

<400> SEQUENCE: 11

Gly Ile Val Asp Gln
1               5
```

```
<210> SEQ ID NO 12
<211> LENGTH: 5
<212> TYPE: PRT
<213> ORGANISM: Rat

<400> SEQUENCE: 12

Cys Cys Thr Ser Ile
1               5

<210> SEQ ID NO 13
<211> LENGTH: 5
<212> TYPE: PRT
<213> ORGANISM: Rat

<400> SEQUENCE: 13

Cys Ser Leu Tyr Gln
1               5

<210> SEQ ID NO 14
<211> LENGTH: 5
<212> TYPE: PRT
<213> ORGANISM: Rat

<400> SEQUENCE: 14

Leu Glu Asn Tyr Cys
1               5

<210> SEQ ID NO 15
<211> LENGTH: 1
<212> TYPE: PRT
<213> ORGANISM: Rat

<400> SEQUENCE: 15

Asn
1

<210> SEQ ID NO 16
<211> LENGTH: 5
<212> TYPE: PRT
<213> ORGANISM: Feline

<400> SEQUENCE: 16

Phe Val Asn Gln His
1               5

<210> SEQ ID NO 17
<211> LENGTH: 5
<212> TYPE: PRT
<213> ORGANISM: Feline

<400> SEQUENCE: 17

Leu Cys Gly Ser His
1               5

<210> SEQ ID NO 18
<211> LENGTH: 5
<212> TYPE: PRT
<213> ORGANISM: Feline

<400> SEQUENCE: 18

Leu Val Glu Ala Leu
1               5

<210> SEQ ID NO 19
<211> LENGTH: 5
```

```
<212> TYPE: PRT
<213> ORGANISM: Feline

<400> SEQUENCE: 19

Val Leu Val Cys Gly
1               5

<210> SEQ ID NO 20
<211> LENGTH: 5
<212> TYPE: PRT
<213> ORGANISM: Feline

<400> SEQUENCE: 20

Glu Arg Gly Phe Phe
1               5

<210> SEQ ID NO 21
<211> LENGTH: 5
<212> TYPE: PRT
<213> ORGANISM: Feline

<400> SEQUENCE: 21

Val Thr Pro Lys Ala
1               5

<210> SEQ ID NO 22
<211> LENGTH: 5
<212> TYPE: PRT
<213> ORGANISM: Rat

<400> SEQUENCE: 22

Phe Val Lys Gln His
1               5

<210> SEQ ID NO 23
<211> LENGTH: 5
<212> TYPE: PRT
<213> ORGANISM: Rat

<400> SEQUENCE: 23

Leu Cys Gly Pro His
1               5

<210> SEQ ID NO 24
<211> LENGTH: 5
<212> TYPE: PRT
<213> ORGANISM: Rat

<400> SEQUENCE: 24

Leu Val Glu Ala Leu
1               5

<210> SEQ ID NO 25
<211> LENGTH: 5
<212> TYPE: PRT
<213> ORGANISM: Rat

<400> SEQUENCE: 25

Val Leu Val Cys Gly
1               5

<210> SEQ ID NO 26
<211> LENGTH: 5
<212> TYPE: PRT
<213> ORGANISM: Rat
```

<400> SEQUENCE: 26

Glu Arg Gly Phe Phe
1               5

<210> SEQ ID NO 27
<211> LENGTH: 5
<212> TYPE: PRT
<213> ORGANISM: Rat

<400> SEQUENCE: 27

Val Thr Pro Lys Ser
1               5

<210> SEQ ID NO 28
<211> LENGTH: 5
<212> TYPE: PRT
<213> ORGANISM: Rat

<400> SEQUENCE: 28

Phe Val Lys Gln His
1               5

<210> SEQ ID NO 29
<211> LENGTH: 5
<212> TYPE: PRT
<213> ORGANISM: Rat

<400> SEQUENCE: 29

Leu Cys Gly Ser His
1               5

<210> SEQ ID NO 30
<211> LENGTH: 5
<212> TYPE: PRT
<213> ORGANISM: Rat

<400> SEQUENCE: 30

Leu Val Glu Ala Leu
1               5

<210> SEQ ID NO 31
<211> LENGTH: 5
<212> TYPE: PRT
<213> ORGANISM: Rat

<400> SEQUENCE: 31

Val Leu Val Cys Gly
1               5

<210> SEQ ID NO 32
<211> LENGTH: 5
<212> TYPE: PRT
<213> ORGANISM: Rat

<400> SEQUENCE: 32

Glu Arg Gly Phe Phe
1               5

<210> SEQ ID NO 33
<211> LENGTH: 5
<212> TYPE: PRT
<213> ORGANISM: Rat

```
-continued

<400> SEQUENCE: 33

Val Thr Pro Met Ser
1               5
```